United States Patent [19]

Shorter et al.

[11] Patent Number: 5,376,137
[45] Date of Patent: Dec. 27, 1994

[54] ARTIFICIAL LEG WITH HYDRAULIC KNEE FLEXION RESISTANCE

[75] Inventors: John J. Shorter, Basingstoke; Vic J. Woolnough, North Waltham; Peter D. Edwards, Northampton, all of England

[73] Assignee: Chas. A. Blatchford & Sons Limited, Basingstoke, England

[21] Appl. No.: 93,797

[22] Filed: Jul. 19, 1993

Related U.S. Application Data

[63] Continuation of Ser. No. 801,036, Dec. 2, 1991, abandoned.

[30] Foreign Application Priority Data

Mar. 14, 1991 [GB] United Kingdom ............... 9105464
Oct. 9, 1991 [GB] United Kingdom ............... 9121417

[51] Int. Cl.$^5$ ........................... A61F 2/64; A61F 2/74
[52] U.S. Cl. ........................................ 623/44; 623/46
[58] Field of Search ........................... 623/26, 39-46

[56] References Cited

U.S. PATENT DOCUMENTS

| | | | |
|---|---|---|---|
| 2,480,856 | 9/1949 | Henschke et al. | 623/26 |
| 2,605,474 | 8/1952 | Oliver | 623/44 X |
| 2,619,652 | 12/1952 | Vesper | 623/26 |
| 2,859,451 | 11/1958 | Mauch | 623/39 |
| 4,065,815 | 1/1978 | Sen-Jung | |
| 5,092,902 | 3/1992 | Adams et al. | 623/26 |

FOREIGN PATENT DOCUMENTS

| | | | |
|---|---|---|---|
| 0025532 | 3/1923 | France | 623/26 |
| 2740804A1 | 3/1978 | Germany | |
| 661131 | 11/1951 | United Kingdom | |
| 0779087 | 7/1957 | United Kingdom | |
| 1221778 | 2/1971 | United Kingdom | |
| 1534181 | 11/1978 | United Kingdom | |
| 2216426 | 10/1989 | United Kingdom | |
| 1225566 | 4/1986 | U.S.S.R. | 623/39 |

OTHER PUBLICATIONS

Paul C. Klopsteg and Philip E. Wilson, "Human Limbs and Their Substitutes", pp. 481, 541–545, 581–587, Hafner Publishing Company, 1968.
Cross-sectional drawing of "S-N-S" Hydraulic knee control system of Mauch Laboratories, Inc.

*Primary Examiner*—David H. Willse
*Attorney, Agent, or Firm*—Fish & Richardson

[57] ABSTRACT

An artificial leg includes a knee mechanism having means for restricting knee flexing movement during the stance phase of the walking cycle. The restricting means includes a piston and cylinder assembly so coupled in the mechanism that the piston is movable in the cylinder with knee flexion and extension. The knee mechanism includes two chassis parts arranged to move relatively to each other when an axial load is applied to the limb. One end of the piston and cylinder assembly is connected to one of the chassis parts while the other chassis part engages a control member coupled to a valve inside the piston and cylinder assembly so that the valve is operated in response to relative load-dependent movements of the chassis parts in order to restrict the flow of fluid and thereby create resistance to knee flexion during the stance phase. The chassis parts are connected together by an anterior pivot joint and are resiliently moveable relative to each other according to applied load. The piston and cylinder assembly is also operable to resist movement during the swing phase of the walking cycle, and the interaction of the knee chassis parts with the control member is arranged so that movement of the member is reduced or does not occur at all for flexion angles greater than a predetermined value between 30° and 40°.

22 Claims, 2 Drawing Sheets

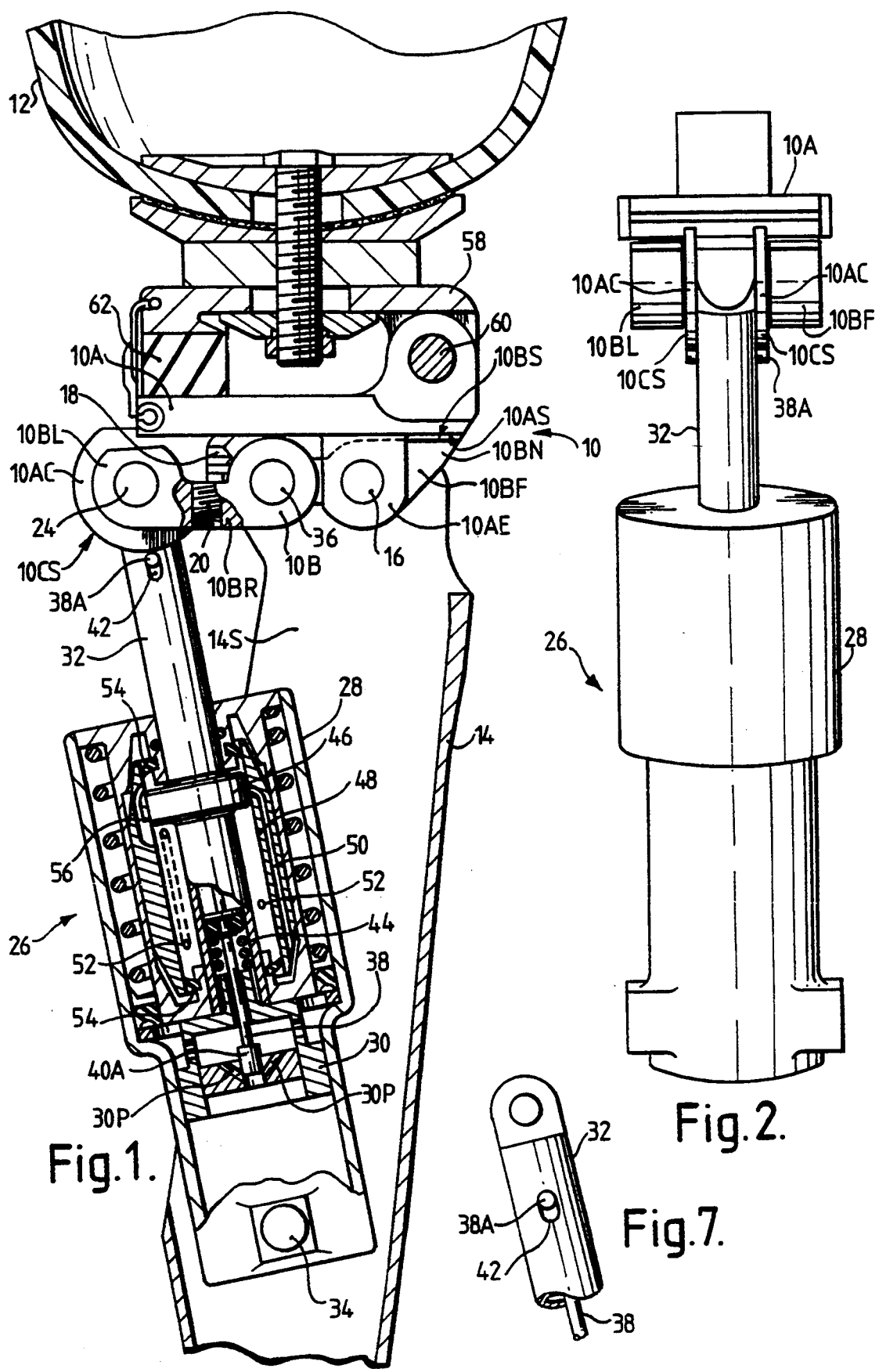

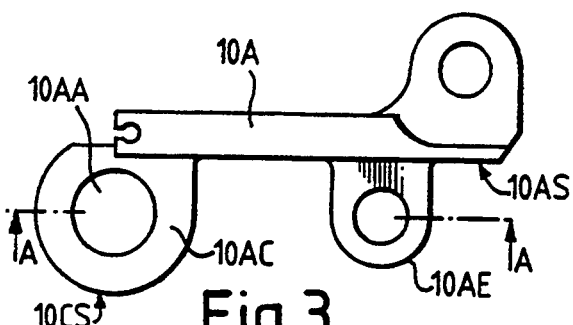
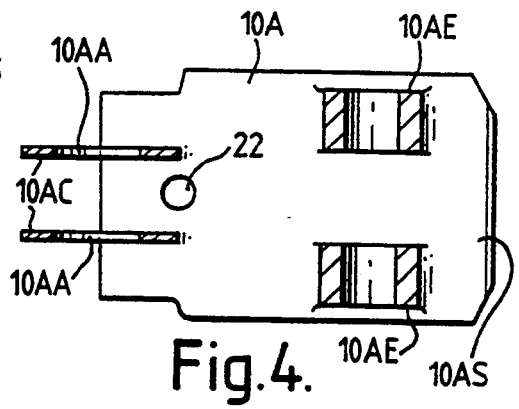
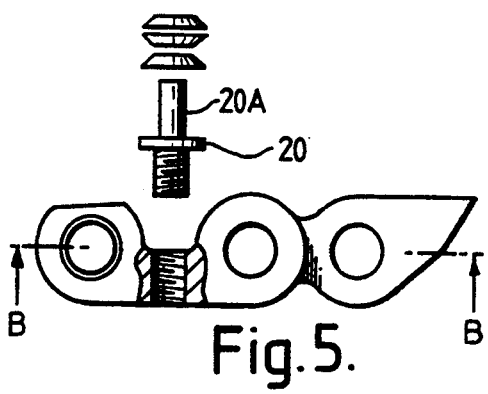
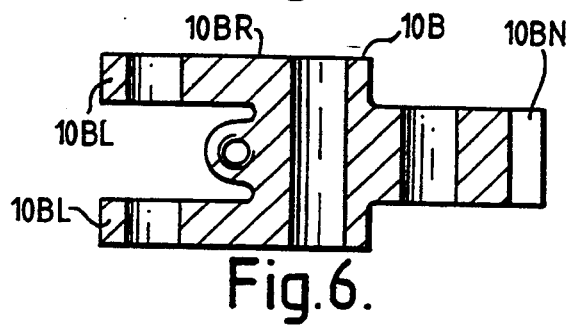
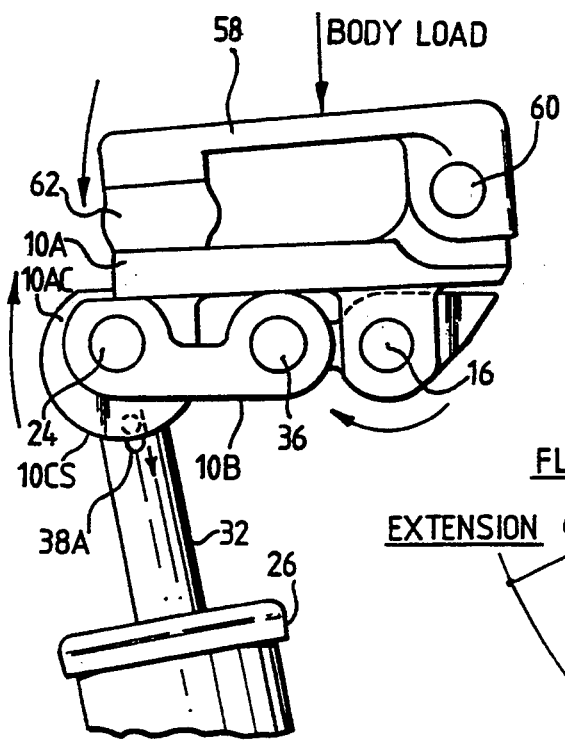
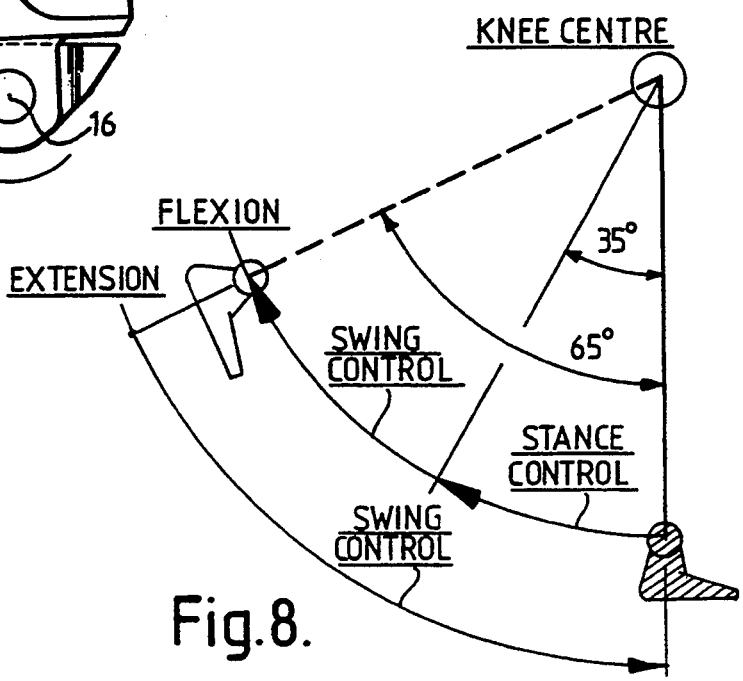

ARTIFICIAL LEG WITH HYDRAULIC KNEE FLEXION RESISTANCE

This is a continuation of application Ser. No. 07/801,036, filed Dec. 2, 1991, now abandoned.

FIELD OF THE INVENTION

This invention relates to an artificial leg including a knee mechanism having means for restricting knee flexion during the stance phase of the walking cycle.

BACKGROUND OF THE INVENTION

It has been well known for a long period of time that one of the important attributes of an artificial leg for achieving a natural-looking walking gait is a so called stabilised knee, i.e. a knee which resists flexion when under load, that is when it is bearing at least some of the weight of the amputee. Purely mechanical devices have been produced such as one including a drum supported on radius arms and encircled by a friction brake band as disclosed in British Patent No. 779087, and one including a drum with an internal brake shoe coupled to a radius arm and a toggle link as shown in British Patent No. 1534181. In both of these devices an axial load on the limb produces a small rotation of the radius arm or arms causing the brake band or brake shoe to grip the drum and to resist knee flexion. Indeed, the resistance may be such that the knee is automatically locked if sufficient load is applied. Often such devices are combined with a pneumatic piston and cylinder assembly which applied lower degrees of resistance to flexion and/or extension of the knee to control the motion of the shin during the swing phase.

It is also known to provide resistance to flexion during the stance phase as well as the swing phase by means of a piston and cylinder assembly. One example of such an arrangement is the hydraulic "S-N-S" knee control system manufactured by Mauch Laboratories, Inc. In some situations, however, this system requires the amputee to make a conscious knee-extending movement before flexion can be initiated.

SUMMARY OF THE INVENTION

According to one aspect of this invention there is provided an artificial leg which has an upper leg component, lower leg component, knee pivoting means pivotally coupling the lower leg component to the upper leg component to permit knee flexion and extension movements, and an hydraulic piston and cylinder assembly coupled between the upper and lower leg components to resist at least the flexion movement during the stance phase. Automatic control means are provided for altering the degree to which the piston and cylinder assembly resist the flexion movement. One of the leg components includes at least two portions, one of which is coupled to the other leg component by the knee pivoting means and is movable relative to the other of the two portions in response to application of an axial load to the one leg component. The control means are responsive to the relative movement of the leg component portions to increase the resistance of the piston and cylinder assembly to the flexion movement when the knee flexion angle is within a first knee flexion angle range, but are comparatively unresponsive in the sense that little or no increase in resistance occurs when the knee flexion angle is within a second knee flexion angle range which is above the first angle range. In this way, knee stability can be obtained with an hydraulic device, to the extent of an hydraulic lock if required, automatically when the patient applies weight during the stance phase. No conscious knee-extending movement needs to be made when resistance to flexion is to be removed, and stance control is available during the initial part of the flexion range when it is needed.

In the preferred embodiment of the invention the one leg component portion is a knee chassis part movably mounted at the distal end of the upper leg component, specifically a stump socket, this chassis part housing a bearing for the lower leg component, specifically the shin, the bearing defining a knee axis of rotation which extends transversely of the leg. Preferably, the one leg component portion is hinged or pivotally connected to the other portion of the upper leg component in an overlapping arrangement with the knee axis spaced from the pivotal connection. By arranging for a resilient element such as an elastic buffer or spring to be compressed when the two portions move with respect to each other in response to application of an axial load, and by locating the pivotable connection so as to be spaced from the knee axis in a direction generally perpendicularly with respect to the longitudinal axis of the leg, the upper leg component-portions can be made to pivot with respect to each other as a function of the load applied to the leg.

Preferably, the piston and cylinder assembly has two ends each pivotally connected to a respective one of the leg components, that end of the assembly which is connected to the one leg component being pivotally connected to one of the two leg component portions. In this case, the control mechanism may include (i) a control member which forms part of the piston and cylinder assembly and which is arranged to engage the other of the two leg component portions, and (ii) a cam associated with the other of the two leg component portions and shaped to reduce or eliminate load-dependent resistance to flexion when the knee flexion angle is in the second knee flexion angle range.

In the preferred embodiment, the assembly has an upper pivot on one of the upper leg component portions at a position behind the knee axis and a lower pivot on the shin some distance below the knee axis. If the other upper leg component portion extends to a point adjacent the upper pivot, its movement relative to the pivot with changing load conditions in the leg may be transmitted by the control means via a control member to a valve which restricts fluid flow in the piston and cylinder assembly. In particular, in the case of the piston and cylinder assembly having a piston rod connected to the upper pivot, the control member may be connected to a second rod running parallel to the piston rod, either inside it or beside it, directly to the valve. The above-mentioned cam on the leg component portion which moves relative to the upper pivot is engaged by the control member so that actuation of the latter is confined to the first knee flexion angle range. The leg component portions may be constructed so as to include knee chassis parts which move relative to each other on application of the axial load.

In an advantageous embodiment of the invention, the piston and cylinder assembly also serves to resist flexion and extension of the knee during the swing phase of the walking cycle. The likelihood of actuation of the control means (comprising the control member and its cooperating members) during the swing phase due to the resistance to swing phase flexion being sufficient to overcome the biasing force of the above-mentioned resilient element is avoided or reduced by the fact that the control means is largely unresponsive within the second knee flexion angle range. This second angle range typically has a lower limit corresponding to a predetermined angle between 30° and 40°, the cam referred to above being shaped accordingly.

The inclusion of means for resisting swing phase flexion can, in some circumstances, affect the removal of flexion resistance in the stance phase, just before toe-off. In order to avoid this difficulty the piston and cylinder assembly may be so constructed that the resistance to flexion provided by the assembly independently of the actuation of the control means for stance control occurs only during part of the swing phase, e.g. only when the knee flexion angle is in the second knee flexion angle range, or when the flexion angle is more than a predetermined angle between 30° and 40°. This can be achieved by providing one or more transfer passages in the piston and cylinder assembly which are shut off when the flexion angle is greater the predetermined angle.

The invention also includes, according to another aspect thereof, a knee mechanism for rotatably connecting a shin component of an artificial leg to a thigh component of the leg, wherein the mechanism comprises: a first part for connection to one of the components; a second part movable relative to the first part in response to the application of an load to the one component, the load being directed axially of the component; knee pivoting means for pivotally coupling the second part to the other of the components; an hydraulic piston and cylinder assembly coupled to one of the said parts and arranged to be coupled to the said other component for resisting flexion movement of the said one component relative to the said other component during the stance phase; and automatic control means for altering the degree to which the piston and cylinder assembly resists the flexion movement; wherein the control means are responsive to the relative movement of the first and second parts of the mechanism to increase the resistance of the piston and cylinder assembly to the flexion movement when the knee flexion angle of the one component with respect to the other component is within a first knee flexion angle range, but are comparatively unresponsive when the knee flexion angle is within a second knee flexion angle range which is above the first angle range.

According to yet a further aspect of the invention, an artificial leg comprises an upper leg component; a lower leg component knee pivoting means pivotally coupling the lower leg component to the upper leg component to permit knee flexion and extension movements; an hydraulic piston and cylinder assembly coupled between the upper and lower leg components to resist at least the flexion movement during the stance phase; and automatic control means for altering the degree to which the piston and cylinder assembly resists the flexion movement, wherein one of the leg components includes at least two portions, one of which is coupled to the other of the leg components by the knee pivoting means and is movable relative to the other of the two portions in response to the application of an axial load to the one leg component; wherein the piston and cylinder assembly has two ends each pivotally connected to a respective one of the leg components, and wherein that end of the assembly which is connected to the one leg component is pivotally connected to the one leg component portion; and wherein the control means are responsive to the load-responsive relative movement of the two leg component portions to increase the resistance of the piston and cylinder assembly to the flexion movement.

In the preferred embodiment the one leg component portion is pivotally attached to the other leg component portion by means of an anterior pivotal connection, and one end of the piston and cylinder assembly is pivotally attached to the one leg component portion at a posterior pivotal connection. As a result, the control means tends not to actuate stance control resistance when a force line representative of ground reaction at the foot passes sufficiently far forward at the level of the knee that the moment tending to actuate the control means is then insufficient to overcome spring bias biasing the knee joint carrier away from the actuating position. This Situation occurs towards the end of the stance phase.

The invention will now be described below by way of example with reference to the drawings.

BRIEF DESCRIPTION OF THE DRAWINGS

In the drawings:

FIG. 1 is a partly sectioned side elevation of part of an artificial leg in accordance with the invention;

FIG. 2 is a rear elevation of part of a knee mechanism shown in FIG. 1;

FIG. 3 is side elevation of an upper chassis part of the mechanism;

FIG. 4 is an underside view of the upper chassis part section on the line A—A in FIG. 3;

FIG. 5 is a partly sectioned side view of a lower chassis part of the knee mechanism;

FIG. 6 is an underside view of the lower chassis part sectioned on the line B—B in FIG. 5;

FIG. 7 is a detail of a piston rod end;

FIG. 8 is a diagram depicting different phases of resistance to knee flexion and extension movements;

FIG. 9 is a side elevation of the knee mechanism shown in FIG. 1, the mechanism being in a loaded condition.

DETAILED DESCRIPTION OF THE PREFERRED EMBODIMENT

Referring to FIGS. 1 to 7, an artificial leg in accordance with the invention has a knee mechanism with a knee chassis 10 having an upper part 10A for connection to an thigh component 12 and a lower part 10B for connection to a shin 14, which are pivotally connected to each other by a transverse front pivot pin 16 housed in two ears 10AE of the upper part 10A and passing through a bore in a front end portion 10BF of the lower part 10B. The lower chassis part 10B extends rearwardly from the front pivot pin 16 to a rear portion 10BR which carries a stack of disc springs 18 on an upright stud 20. This stud 20 has an upper end 20A (FIG. 5) which projects beyond the spring stack 18 and is received in a bore 22 (FIG. 4) in the upper chassis part 10A. Rearwardly of the spring stack 18, the lower chassis part rear portion is divided into two lugs 10BL each bored to accept a rear pivot pin 24. Adjacent the inner faces of the lugs 10BL are two cam plates 10AC depending from the upper chassis part 10A which is contiguous and overlapping with respect to the lower chassis part 10B. It will be seen that the lower chassis part 10B is free to pivot on the front pivot pin 16 subject to the resistance provided by the spring stack 18 bearing against the underside of the upper chassis part, with the lugs 10BL moving up or down relative to the cam plates 10AC. An aperture 10AA (FIG. 3) is cut in each cam plate 10AC to allow sufficient clearance around the rear pivot pin 24 for such movement. A front nose portion 10BN of the lower chassis part 10B extends forwardly of the front pivot pin 16 and has an upper stop surface 10BS which is positioned so as to bear against a lower stop surface 10AS of the upper chassis part 10 to limit the extent to which the two chassis parts can move apart.

The knee mechanism also includes a piston and cylinder assembly 26 with a cylinder body 28, a main piston 30, and a hollow piston rod 32. The latter is secured to the rear pivot pin 24 between the cam plates 10AC, while the cylinder body has pivot axles 34 projecting from its lower end for pivotal housing in the shin 14 of the limb. In this embodiment of the invention the upper end of the shin 14 has two side pieces 14S attached to a knee axis bearing pin 36 housed in the lower chassis part 10B. Consequently, the piston and cylinder assembly 26 forms one side of a triangle defined by the knee axis pin 36, the rear pivot pin 24 and the pivot axles 34.

As the knee flexes, the piston 30 moves downwardly in the cylinder body 28. When the amputee applies weight to the leg, a longitudinally directed force on the shin 14 is applied to the knee axis bearing pin 36, causing the lower chassis part 10B to move towards the upper chassis part 10A provided that the force is sufficient that the spring stack 18 can be compressed. As a result the upper end of the piston rod 32, secured to the rear pivot pin 20, moves upwardly between the cam plates 10AC. The piston rod 32 houses a slidable coaxial control rod 38 acting as a valve control member for a valve 40 housed in the main piston 30. The upper end of the control rod 38 carries a cross pin 38A which penetrates the wall of the piston rod 32 through slots 42 to emerge on both sides adjacent cam surfaces 10CS of the cam plates 10AC. In fact, a spring 44 inside the piston rod 32 biases the control rod 38 upwardly into contact with the cam surfaces 10CS so that as the knee flexes the pin 38A follows the cam surfaces providing it does not reach the ends of the slots 42. It will now be understood that upward movement of the lower chassis part 10B due to application of the amputee's weight causes downward movement of the control rod 38 with respect to the piston 30. A valve member 40A secured to the lower end of the control rod 38 is arranged to close off progressively passages 30P connecting one side of the piston 30 to the other as the control rod 38 moves downwardly in the piston rod 32, thereby restricting fluid flow through the piston 30 to the extent that, when the valve 40 is fully closed, an hydraulic lock results, thereby locking the knee.

The relative positions of the pivots defined by pins 16, 36 and 24, together with the position and stiffness of the spring stack 18, determine the locking characteristics of the mechanism. In this embodiment the front pivot, defined by pin 16, is in front of the knee axis by a predetermined distance with the result that the lower chassis part 10B will tend to move towards the upper chassis part 10A so long as there is a resultant reaction force from the ground through the foot and directed to the rear of the front pivot. Provided then that the predetermined distance is sufficiently large and the spring stack stiffness is sufficiently low, upward movement of the lower chassis part will occur and the control rod 38 in the piston and cylinder assembly 26 will move to restrict and, in the limit, prevent knee flexion. In practice, the reaction force satisfies these conditions during the major part of the stance phase, in fact from heel contact to shortly before toe-off.

As the amputee's body moves forward over the foot, the resultant reaction force is directed along a line which is moving progressively further forward until the moment on the lower chassis part due to the applied load is insufficient to overcome the biasing force of the spring stack, and the stance control resistance consequently diminishes until it is removed altogether before toe-off.

Preferably, the mechanism is arranged such that application of a hip torque tending to extend the knee when the leg is bearing the amputee's weight causes the lower chassis part 10B to move away from the upper chassis part 10A so as to remove the stance control resistance and allow knee extension. In some circumstances, however, such a characteristic is difficult to achieve and a non-return valve (not shown) may be included associated with the piston 30 to provide a bypass passage from the space above the piston to the space below to allow extension of the knee when the valve 40 is closed or partly closed.

The piston and cylinder assembly 26 has a secondary piston 46 mounted inside an internal secondary cylinder 48. This secondary piston 46 is fixed to the same piston rod 32 as the main piston 30 and they therefore move together. Passages 50 connect the fluid spaces 52, 54 on either side of the secondary piston 46. In fact, the walls of the secondary cylinder 48 are perforated at various longitudinal positions, the apertures 52 so formed connecting with the passages 50 leading to one end or other of the cylinder 48 via non-return valves 54. The arrangement is such that on a downward stroke of the piston 46, resistance to movement of the piston at any given position in its stroke is governed by the total orifice area defined by those of the apertures 52 which remain uncovered below the piston and which connect via passages 50 to the top of the cylinder 48. Similarly, on the upward stroke, at any point in the stroke the resistance is governed by the orifice area represented by the uncovered apertures 52 above the piston 46 and connected via passages 50 to the bottom end of the cylinder 48. It will be appreciated that by selecting the sizes and positions of the perforations, the resistance to movement can be varied so as to be different at different parts of the upward stoke and the downward stoke respectively.

Since the operation of the secondary piston 46 and cylinder 48 is independent of the position of the valve 40, they resist flexion and extension regardless of whether the leg is weight-bearing or not. In effect they operate as a swing phase control device.

Under certain conditions the pivoting force applied to the lower chassis part 10B due to resistance on the secondary piston 46 during flexion of the knee may be sufficient to compress the spring stack 18 and thereby activate the hydraulic lock. This is most likely to occur at or shortly after toe-off. To avoid such lock activation, the cam surfaces 10CS are shaped so that their radius with respect to the axis of the rear pivot pin 24 is reduced for angles of flexion greater than about 30° to 40°, preferably 35°. The reduction in radius is arranged to prevent significant movement of the control rod 38 when the chassis parts 10A and 10B move together and when the flexion angle is greater than this amount. This prevents an adverse effect of the main piston 30, the function of which is stance control, on swing control.

During the initiation of flexion prior to toe-off, the stance control resistance, i.e. the hydraulic lock, is normally progressively removed as weight is transferred to the other leg. This normally occurs well below the 35° flexion angle referred to above. To avoid any unwanted hindering of such removal of stance control due to forces generated by the secondary piston 46, the function of which is swing control, a passage 56 opens out into the upper part of the wall of the cylinder 48 to provide a large orifice area at the beginning of the downward stroke of the piston 46. The passage 56 links the cylinder space below the piston 46 to the space above the piston either directly, as shown in FIG. 1, or via a non-return value if cushioning towards the end of the extension stroke is to be retained. As a result, the resistance to flexion provided by the piston 46 during the initiation of flexion, preferably during the first 35° of flexion, is very low, and resistance is provided mainly by the main piston 30 subject to weight-activation via control rod 38. Thus, the swing control is prevented from adversely affecting the stance control.

The result of these measures is that stance control is largely separated from swing control, at least during flexion, to avoid unwanted operation of the stance control mechanism. This is shown diagrammatically in FIG. 8. During flexion when the knee flexion angle is in a first knee flexion angle range, typically between 0° and 35° flexion, only the stance control mechanism (including main piston 30) is operative, depending on the loads applied to the leg. The swing control mechanism (including piston 46) is substantially ineffective in this range. In the latter stage of flexion, when the flexion angle is within a second knee flexion angle range, typically extending upwards from 35°, the stance control mechanism is largely inoperative due to the profile of the cam surface 10CS, and flexion is resisted only by the swing control mechanism. On extension, resistance to movement is exclusively provided by the swing control mechanism throughout both knee flexion angle ranges, as shown in FIG. 8.

The knee mechanism described above may incorporate a stance cushioning device as shown in FIGS. 1 and 9. In this case the thigh component 12 is connected to a top plate 58 which is hinged at its anterior edge to the upper chassis part 10A by a pivot pin-60. A buffer 62 or spring is placed between the posterior portion of the plate 58 and the upper chassis part 10A. Such a combination allows some flexion at the knee while the knee mechanism is locked during the stance phase. Comparison of FIGS. 1 and 9 shows not only the compression of the buffer 62 in the weight-bearing condition, but also the relative approaching movement of the chassis parts 10A, 10B and the operation of the cross pin 38A.

Depending on the degree of stance cushioning required, it is possible for the spring stack 18 (FIGS. 1 and 5) to act as a cushioning device as well as a means of releasing the control rod 38 (FIGS. 1 and 7). In other words, a single pair of relatively movable portions and a single resilient element may perform both functions, in contrast to the arrangement shown in FIGS. 1 and 9.

What is claimed is:

1. An artificial leg comprising:
   an upper leg component,
   a lower leg component,
   knee pivoting means pivotally coupling the lower leg component to the upper leg component to permit knee flexion and extension movements,
   an hydraulic piston and cylinder assembly coupled between said upper and lower leg components to resist at least said flexion movement during the stance phase, and
   automatic control means for altering the degree to which the piston and cylinder assembly resists the flexion movement,
   wherein one of said leg components includes at least two portions, one of which is coupled to the other of said leg components by said knee pivoting means and is movable relative to the other of said two portions in response to the application of an axial load to said one leg component, and
   wherein the control means are responsive to said relative movement of said leg component portions to increase the resistance of said piston and cylinder assembly to said flexion movement when the knee flexion angle is within a first knee flexion angle range, but are comparatively unresponsive when the knee flexion angle is within a second knee flexion angle range which is above said first angle range.

2. An artificial leg according to claim 1, wherein the piston and cylinder assembly has two ends each pivotally connected to a respective one of the leg components, wherein that end of said assembly which is connected to said one leg component is pivotally secured to said one leg component portion, and wherein the control means include a control member forming part of said piston and cylinder assembly and arranged to engage said other leg component portion.

3. An artificial leg according to claim 1, wherein said one leg component portion is pivotally attached to said other leg component portion by means of an anterior pivotal connection, and wherein the piston and cylinder assembly has two ends one of which is pivotally connected to said one leg component portion by means of a posterior pivotal connection and the other of which is pivotally connected to said other leg component.

4. An artificial leg according to claim 1, further comprising a resilient element coupling the two leg component portions and arranged to resist the load-responsive relative movement of the two portions.

5. An artificial leg according to claim 1, wherein:
   said one leg component is the upper leg component,
   said one leg component portion is a knee joint carrier,
   said knee pivoting means comprising a fixed pivot joint carried by said knee joint carrier and defining a knee axis of rotation,
   said knee joint carrier is pivotally attached to said other leg component portion by means of a pivotal connection spaced from the knee axis, and
   the upper leg component includes a resilient element arranged to be compressed when the knee joint carrier moves relative to said other portion of said two leg component portions upon application of an axial load.

6. An artificial leg according to claim 5, wherein:
   the piston and cylinder assembly has two ends each pivotally connected to a respective one of the leg components,
   the pivotal connection between said two portions of said upper leg component defines a pivot axis substantially parallel to and to the anterior of the knee axis,
   that end of the piston and cylinder assembly connected to the upper leg component is pivotally connected to the knee joint carrier to the posterior of the knee joint axis, and the control means include a control member which forms part of said piston and cylinder assembly and which is engaged by said other portion of said two upper leg component portions adjacent the pivotal connection of the piston and cylinder assembly to the knee carrier.

7. An artificial leg according to claim 6, wherein the control member is associated with a control rod running parallel to a piston rod of the piston and cylinder assembly, the control rod being coupled to a valve in the assembly for restricting fluid flow in the assembly.

8. An artificial leg according to claim 5, wherein said other portion of said two leg component portions is itself pivotally attached by means of an anterior pivot connection to a third portion of the upper leg component located proximally with respect to said one and said other portions, said third portion being resiliently coupled to said other portion to the posterior of said anterior pivot connection to provide knee resilience during the stance phase.

9. An artificial leg according to claim 1, wherein the piston and cylinder assembly includes means fur resisting flexion movement of the lower leg component relative to the upper leg component during the swing phase.

10. An artificial leg according to claim 9, including means for reducing the resistance of the piston and cylinder assembly to flexion movement during the swing phase when the knee flexion angle is within said first angle range in comparison to the resistance to swing phase flexion when the flexion angle is within said second angle range.

11. An artificial leg according to claim 10, wherein said first and second angle ranges extend respectively below and above a predetermined knee flexion angle in the region of 30° to 40°.

12. An artificial leg according to claim 11, wherein said means for reducing resistance to flexion comprises at least one transfer passage in the piston and cylinder assembly, which passage is restricted when the flexion angle is greater than said predetermined angle.

13. An artificial leg according to claim 1, wherein said control means include means for progressively reducing said resistance to flexion movement with increasing angles of knee flexion.

14. An artificial leg according to claim 1, wherein:
the piston and cylinder assembly has two ends each pivotally connected to a respective one of the leg components,
that end of said assembly which is connected to said one leg component is pivotally connected to one of said two leg component portions,
the control means include (i) a control member which forms part of the piston and cylinder assembly and which is arranged to engage the other of said two leg component portions, and (ii) a cam associated with said other of said two leg component portions and shaped to reduce said resistance to flexion with increasing knee flexion angle.

15. An artificial leg according to claim 14, wherein:
said piston and cylinder assembly is coupled to said one leg component by a piston rod of the assembly,
said control member extends transversely from the piston rod and is associated with a control rod running parallel to said piston rod and coupled to a valve for restricting fluid flow in the assembly, and said cam is located alongside said piston rod to engage the control member.

16. A knee mechanism for rotatably connecting a shin component of an artificial leg to a thigh component of the leg, wherein the mechanism comprises:
a first part for connection to one of said components,
a second part movable relative to said first part in response to the application of a load to said one component, the load being directed axially of the component,
knee pivoting means for pivotally coupling the second part to the other of said components,
an hydraulic piston and cylinder assembly coupled to one of the said parts and arranged to be coupled to said other component for resisting flexion movement of said one component relative to said other component during the stance phase, and
automatic control means for altering the degree to which the piston and cylinder assembly resists the flexion movement,
wherein the control means are responsive to said relative movement of said first and second parts of the mechanism to increase the resistance of said piston and cylinder assembly to said flexion movement when the knee flexion angle of said one component with respect to said other component is within a first knee flexion angle range, but are comparatively unresponsive when said knee flexion angle is with a second knee flexion angle range which is above the first angle range.

17. An artificial leg comprising:
an upper leg component;
a lower leg component;
knee pivoting means pivotally coupling the lower leg component to the upper leg component to permit knee flexion and extension movements,
an hydraulic piston and cylinder assembly coupled between said upper and lower leg components to resist at least said flexion movement during the stance phase, and
automatic control means for altering the degree to which the piston and cylinder assembly resists the flexion movement,
wherein one of said leg components includes at least two portions, one of which is coupled to the other of said leg components by said knee pivoting means and is configured to move generally in the direction of a longitudinal axis of said one leg component relative to the other of said two portions in response to the application of an axial load to said one leg component in the direction of said longitudinal axis,
wherein the piston and cylinder assembly has two ends each pivotally connected to a respective one of the leg components, and wherein that end of said assembly which is connected to said one leg component is pivotally connected to said one leg component portion; and
wherein the control means are responsive to said load-responsive relative movement of the two leg component portions to increase the resistance of said piston and cylinder assembly to said flexion movement.

18. An artificial leg according to claim 17, wherein said one leg component portion is pivotally attached to said other leg component portion by means of an anterior pivotal connection, and wherein the piston and cylinder assembly has two ends one of which is pivotally connected to said one leg component portion by means of a pivotal connection to the posterior of said knee pivoting means and the other of which is pivotally connected to said other leg component.

19. An artificial leg according to claim 18, wherein:
said one leg component is the upper leg component,
said one leg component portion is a knee joint carrier,
said knee pivoting means comprising a fixed pivot joint carried by said knee joint carrier and defining a knee axis of rotation,
said knee joint carrier is pivotally attached to said other leg component portion by means of a pivotal connection spaced anteriorly from the knee axis, and the upper leg component includes a resilient element arranged to be compressed when the knee joint carrier moves relative to said other portion of said two leg component portions upon application of an axial load.

20. An artificial leg according to claim 19, wherein the knee axis is between said anterior and said posterior connections.

21. An artificial leg according to claim 17, wherein the other end of said piston and cylinder assembly is connected at a fixed pivot on said other leg component.

22. An artificial leg according to claim 17, wherein said end of said piston and cylinder assembly is pivotally connected to said one leg component portion at a position spaced from the knee pivoting means.

* * * * *